(12) United States Patent
Williams

(10) Patent No.: US 6,952,161 B1
(45) Date of Patent: *Oct. 4, 2005

(54) MOTOR VEHICLE EMERGENCY SYSTEM

(76) Inventor: Joy A. Williams, 5417 Alfred Dr., Las Vegas, NV (US) 89108

( * ) Notice: Subject to any disclaimer, the term of this patent is extended or adjusted under 35 U.S.C. 154(b) by 24 days.

This patent is subject to a terminal disclaimer.

(21) Appl. No.: 10/423,509

(22) Filed: Apr. 24, 2003

(51) Int. Cl.$^7$ .................................................. B60Q 1/22
(52) U.S. Cl. ...................................... 340/463; 340/439
(58) Field of Search ................................ 340/463, 464, 340/439, 576; 180/272

(56) References Cited

U.S. PATENT DOCUMENTS

| | | | |
|---|---|---|---|
| 5,465,079 A * | 11/1995 | Bouchard et al. ............ 340/576 |
| 5,706,909 A | 1/1998 | Bevins et al. |
| 5,793,292 A * | 8/1998 | Ivey, Jr. ....................... 340/576 |
| 5,805,057 A | 9/1998 | Eslaminovin |
| 5,838,227 A | 11/1998 | Murray |
| 5,942,979 A * | 8/1999 | Luppino ...................... 340/576 |
| 5,990,795 A * | 11/1999 | Miller ......................... 340/576 |
| 6,167,746 B1 * | 1/2001 | Gammenthaler ............ 73/19.01 |
| 6,184,791 B1 * | 2/2001 | Baugh ......................... 340/576 |
| 6,239,707 B1 * | 5/2001 | Park ............................ 340/576 |
| 6,252,978 B1 * | 6/2001 | Grantz ........................ 382/118 |
| 6,297,732 B2 * | 10/2001 | Hsu et al. .................... 340/439 |
| 6,522,246 B1 | 2/2003 | Williams |
| 6,542,081 B2 * | 4/2003 | Torch .......................... 340/575 |
| 2002/0120374 A1 * | 8/2002 | Douros et al. ................. 701/29 |
| 2002/0121981 A1 * | 9/2002 | Munch ........................ 340/576 |
| 2002/0175015 A1 * | 11/2002 | Michaud et al. ............ 180/272 |
| 2003/0011481 A1 * | 1/2003 | Bjorkman .................... 340/576 |
| 2004/0085211 A1 * | 5/2004 | Gotfried ...................... 340/576 |

* cited by examiner

Primary Examiner—Jeffery Hofsass
Assistant Examiner—Jennifer Stone
(74) Attorney, Agent, or Firm—Robert Ryan Morishita; Anderson & Morishita, LLC

(57) ABSTRACT

The present invention is an emergency system for a motor vehicle. The emergency system includes a monitor collecting data from a driver. The data are transmitted to a data processor that compares the data to baseline standards stored at an associated data structure. If the data deviate from the baseline standards, the data processor actuates a control switch to disable the motor vehicle. In an optional embodiment, the control switch also controls a lamp that is actuated simultaneously with the disabling means. In a further optional embodiment, the lamp and disabling means are separately controlled.

19 Claims, 4 Drawing Sheets

MOTOR VEHICLE EMERGENCY SYSTEM

FIELD OF THE INVENTION

The present invention relates to emergency controls for motor vehicles. Specifically, the present invention is a system of automatically actuated means for disabling the motor vehicle to thereby arrest the movement of the motor vehicle in the event of an emergency.

BACKGROUND OF THE INVENTION

Frequently, drivers in motor vehicles become incapacitated or otherwise unable to safely drive while driving. In such a situation, the driver often loses control of his or her motor vehicle and collides with another motor vehicle or leaves the road. In either instance, the driver could be seriously injured and could cause the injury or death of another.

Many attempts have been made to address these problems. For example, motor vehicles now come standard with emergency tail lights to alert other vehicles that the motor vehicle or the driver is disabled. However, one drawback of such systems is that the switch only illuminates the blinking emergency tail lights—the switch does not stop or otherwise slow the motor vehicle.

There are also a variety of means of cutting off the flow of fuel to the motor vehicle engine. These so-called "kill switches" are used in, and controlled by, some anti-theft systems to prevent theft of the motor vehicle. However, such "kill switches" are typically not used to stop the motor vehicle in the event of an emergency. Moreover, such "kill switches" do not include visible or audible warnings to other motorists to indicate that the driver may not have control of the motor vehicle and that the motor vehicle has been disabled.

Yet another system includes a locator device that is monitored by a centralized monitoring system. When assistance is required, the vehicle is located by the monitoring system and assistance is dispatched. One drawback of this system, however, is that the vehicle owner must subscribe to a service to participate in the monitoring system.

In my prior patent, U.S. Pat. No. 6,522,246, I disclosed a system that was manually actuatable to disable a motor vehicle. However, drivers may not always have the time or presence of mind to disable their own motor vehicle. That is, in many situations, the driver may have no warning before becoming unable to drive or the driver may not be aware that he or she is unable to drive. Therefore, there is a need in the art for a system for disabling a vehicle automatically based on data collected from a driver.

SUMMARY OF THE INVENTION

The present invention is an emergency system for a motor vehicle of the type having an electrical system and an engine providing power to the drive wheels of the motor vehicle. The emergency system includes a control switch communicating to a data processor. The data processor includes an associated data structure storing baseline standards. A monitor communicates with the data processor and receives data from the driver of the motor vehicle. Optionally, the monitor is embedded into the motor vehicle in contact with the driver such as in the seat, seat belt, steering wheel, or the like.

Means for disabling the motor vehicle communicate with the data processor. The disabling means could take a variety of forms including a fuel cutoff switch, an ignition switch, an electrical system switch, or the like. The data processor receives data from the monitor about the driver and compares the data to the baseline standards. If the data deviate from the baseline standards, the data processor actuates the disabling means to disable the motor vehicle. For example, the monitor may collect heart activity data from the driver. If the heart activity deviates from the baseline standards, i.e. the heart activity becomes abnormal, the data processor actuates the disabling means.

In an optional embodiment, the emergency system further includes at least one internal lamp, optionally mounted on the interior ceiling of the passenger compartment or near one or more of the doors of the motor vehicle. The lamp or lamps are electrically connected to the motor vehicle's electrical system. Optionally, the lamp or lamps are colored blinking lamps. In a further optional embodiment, the lamp communicates with the control switch such that when the control switch is actuated, the lamp and the disabling means are simultaneously activated. In an alternate optional embodiment, the disabling means and lamp may be separately controlled.

DESCRIPTION

Figure 1:
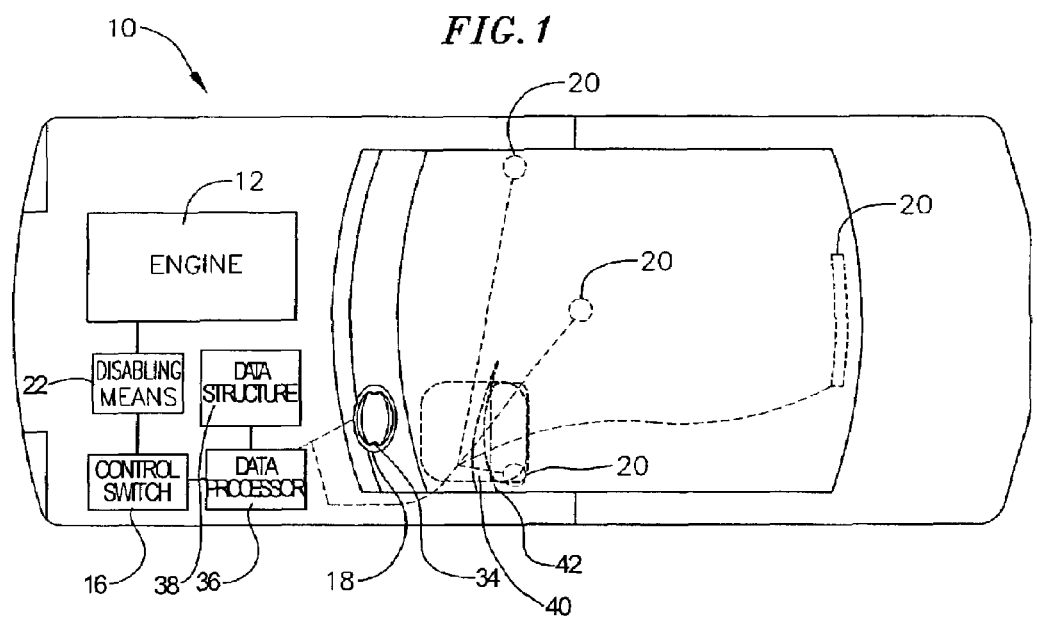
FIG. 1 is a top view of the emergency system of the present invention inside a motor vehicle.
Figure 3:
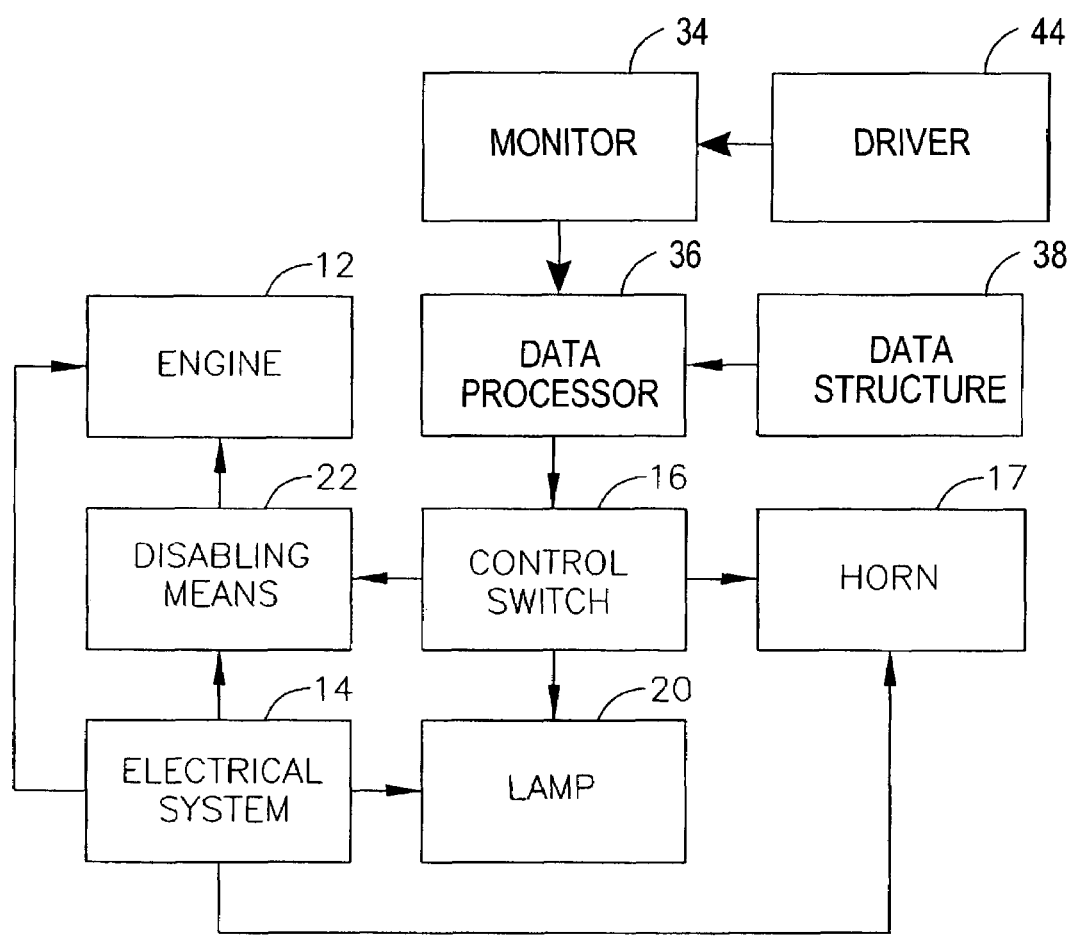
FIG. 3 is a block diagram of an emergency system according to an embodiment of the present invention.

Reference is now made to the figures wherein like parts are referred to by like numerals throughout. With reference to FIGS. 1 and 3, the present invention is an emergency system for a motor vehicle 10. The motor vehicle 10 is of a type having an engine 12 and an electrical system 14. The engine 10 could be any type known in the art including spark ignition, compression ignition, electrical, or the like, the purpose of which is to provide drive power to the motor vehicle's 10 wheels. The motor vehicle 10 could be of any type known in the art including a car, truck, van, bus, or any other type of motor vehicle 10.

Likewise, the electrical system 14 could be of any type known in the art for operating electrical devices in the motor vehicle 10 as well as assisting in starting the motor vehicle's 10 engine 12. For example, the electrical system 14 could be a conventional electrical system 14 having a battery, or other electricity storage device, and an alternator or generator to recharge the battery and provide electricity when the engine 10 is running.

The device of the present invention includes a control switch 16 electrically connected to the electrical system 14. While in one optional embodiment, the control switch 16 is manually actuatable, it does not necessarily need to be manually actuatable. That is, the control switch 16 may merely be a switch actuating the circuit controlling the disabling means 22 discussed below.

A data processor 36 communicates with the control switch 16. The data processor 36 includes an associated data structure 38, such as a data memory. The data memory could take many different forms including read-only memory ("ROM"), random access memory ("RAM"), optical memory, magnetic memory, electrically alterable read-only memory ("EAROM"), electrically programmable read-only memory ("EPROM"), electrically erasable programmable read only memory ("EEPROM"), or any other form of data structure 38. The data structure 38 stores baseline standards. The data structure 38 may store additional data such as instructions for executing the functions described herein.

A monitor 34 communicates with the data processor 36 and collects data from the driver 44 of the motor vehicle. It is noted that more than one monitor 34 may be used. Also, it is contemplated that each monitor 34 may collect more than one type of data. The data collection may be passive and may take many forms. For example, heart data, brain data, muscle data, or the like may be collected by the monitor 34 and transmitted to the data processor 36. To make the monitor 34 unobtrusive, the monitor 34 may be embedded into the motor vehicle, such as in, a seat 40, the steering wheel, the seat belt 42, or anywhere else in contact with the driver. Alternatively, the monitor 34 may be attached to the body or clothing of the driver, such as using a wired or wireless clip, lead, electrode, or the like to the driver's body.

Referring again to FIGS. 1 and 3, the control switch 16 controls a means 22 for disabling the motor vehicle 10. The disabling means 22 may take many different forms. Regardless of the specific configuration of the disabling means 22, the disabling means 22 is connected to the motor vehicle 10 and the control switch 16. In one optional embodiment, the disabling means 22 is a fuel cutoff valve that stops the flow of fuel from the motor vehicle fuel system to the engine 12 to thereby disable the engine 12. Alternatively, in a spark ignition engine, the disabling means 22 could include an ignition switch that prevents the electrical system 14 from sending electricity to the spark plugs, thereby disabling the engine 12. Similarly, in an electric motor vehicle, the disabling means 22 could include an electrical system 14 switch to cease the flow of electricity to the engine 12. In yet another optional embodiment, the disabling means 22 may also be connected to the motor vehicle's 10 brakes. Thus, the disabling means 22 could actuate the brakes or otherwise slow the motor vehicle 10 when the control switch 16 is actuated.

In use, data collected by the monitor 34 are communicated to the data processor 36. The data collection may be continuous, periodic, or intermittent. The data processor 36 compares the data to the baseline standards stored at the data structure 38. The data processor 36 prompts the control switch 16 to activate the disabling means 22 when the data deviate from the baseline standards. That is, if the comparison between the data and the baseline standards indicate that the driver's condition is not normal, the data processor 36 signals the control switch 16 to disable the motor vehicle using the disabling means 22. For example, a deviation from the baseline standards could occur in a number of circumstances ranging from unexpected illness, heart attack, seizure, or, in one optional embodiment, intoxication or the influence of drugs.

As the disabling means 22 disables the motor vehicle 10, the motor vehicle 10 slows and stops. As noted above, the disabling means 22 may disable the engine or merely stop the motor vehicle using the brakes. After the motor vehicle 10 ceases its forward motion, or after a preset period of time, or after manual deactivation, the control switch 16 resets itself and deactivates the disabling means 22. The motor vehicle's 10 engine 12 may then be restarted and the motor vehicle 10 may be safely driven.

In an optional embodiment, the control switch 16 additionally controls a lamp 20. That is, in such an optional embodiment, the control switch 16 is electrically connected to the lamp 20 and disabling means 22 such that the lamp 20 and disabling means 22 are simultaneously activated when the control switch 16 is actuated. In an alternate embodiment, the disabling means 22 and lamp 20 are separately controlled.

The lamp 20 could be any visible signal known in the art. In one optional embodiment, the lamp 20 is an exterior lamp. In an alternate optional embodiment, the lamp 20 is mounted in the passenger compartment in the interior of a motor vehicle. In an optional embodiment, the lamp 20 is a blinking colored lamp to distinguish the lamp 20 from the dome light in the interior of the motor vehicle 10 as well as provide enough illumination to be readily visible from outside the motor vehicle 10. In one optional embodiment, the lamp 20 is mounted near the center of the interior ceiling of the motor vehicle 10. In an alternate optional embodiment, the lamp 20 is mounted on the interior ceiling near one or both of the doors of the motor vehicle 10. In a further optional embodiment, a plurality of lamps 20 may be provided with each lamp 20 on the interior ceiling near each door of the motor vehicle 10. Optionally, the lamp 20 may be mounted near or in the rear window of the motor vehicle 10. For example, the lamp 20 may be embedded in the material of the rear window or may overlay the rear window in a fashion similar to embedded or overlaying defrosters known in the art. Optionally the control switch 16 may also be electrically connected to the motor vehicle's 10 horn 17 to thereby issue an audible warning when the control switch 16 is actuated.

Figure 2:
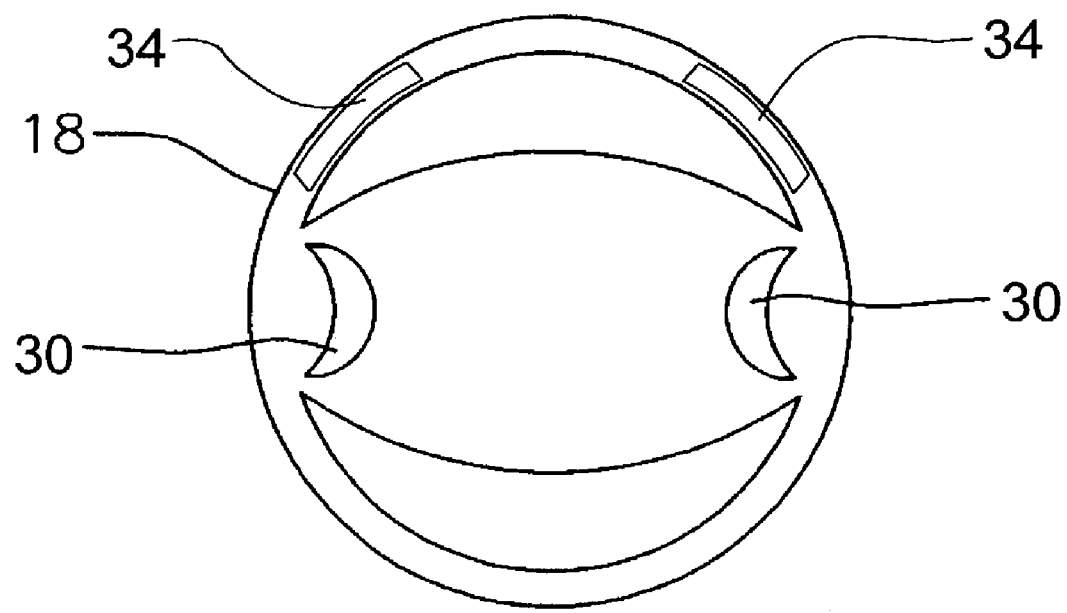
FIG. 2 is a front view of a steering wheel of the present invention with a control switch mounted thereon.

In a further optional embodiment, a manually actuatable second control switch 30 is mounted where the driver and, optionally, the passenger may easily access the second control switch 30. Such an optional second control switch 30 would provide the driver or passenger with a manual means for actuating the lamp 20, disabling means 22, or both. As shown in FIG. 2, the second control switch 30 may optionally be mounted on the steering wheel 18 of the motor vehicle 10. In such an embodiment, the second control switch 30 may optionally be mounted near the perimeter of the steering wheel 18 where it does not interfere with the driver's ability to control the motor vehicle 10, yet is easily accessible in the event of an emergency.

In yet a further embodiment, a manually actuatable third control switch 32 may control only the lamp 20. It should also be noted that the control switch 16, second control switch 30, and third control switch 32 may not necessarily be mutually exclusive. For example, in one optional embodiment, it is contemplated that one system could include all three with a control switch 16 automatically activating the disabling means 22 and lamp 20, a second control switch 30 manually actuatable to activate the disabling means 22 and lamp 20, and a third control switch 32 manually actuatable to activate the lamp 20 only. In this fashion, a control switch would automatically operate to disable the vehicle if the driver data indicates an abnormality, a second control switch 30 could be used to actuate the lamp 20 and disabling means 22 to signal other drivers and stop the motor vehicle 10 in the event of a medical or other emergency, and a third control switch 32 could be used to actuate the lamp 20 to signal a hazard condition, such as inclement weather, an accident, a traffic stoppage, or the like. This embodiment is shown in FIG. 4 and described in more detail below.

In an optional embodiment including a manually actuatable second control switch 30, the second control switch 30 may be actuated in the event of emergency. For example, the second control switch 30 could be actuated if a driver becomes physically or mentally disabled or incapacitated, such as in the event of a seizure, heart attack, or other illness. In an embodiment including a lamp 20, the second control switch 30 activates the lamp 20 and simultaneously activates the disabling means 22. The lamp 20 illuminates, optionally in a blinking fashion to warn oncoming traffic and trailing traffic of the disability or incapacitation of the driver and allow surrounding traffic to react accordingly. Likewise, the visible warning issued by the lamp 20 may indicate that the driver requires assistance and thereby prompt drivers in nearby motor vehicles to call for assistance.

Figure 4:
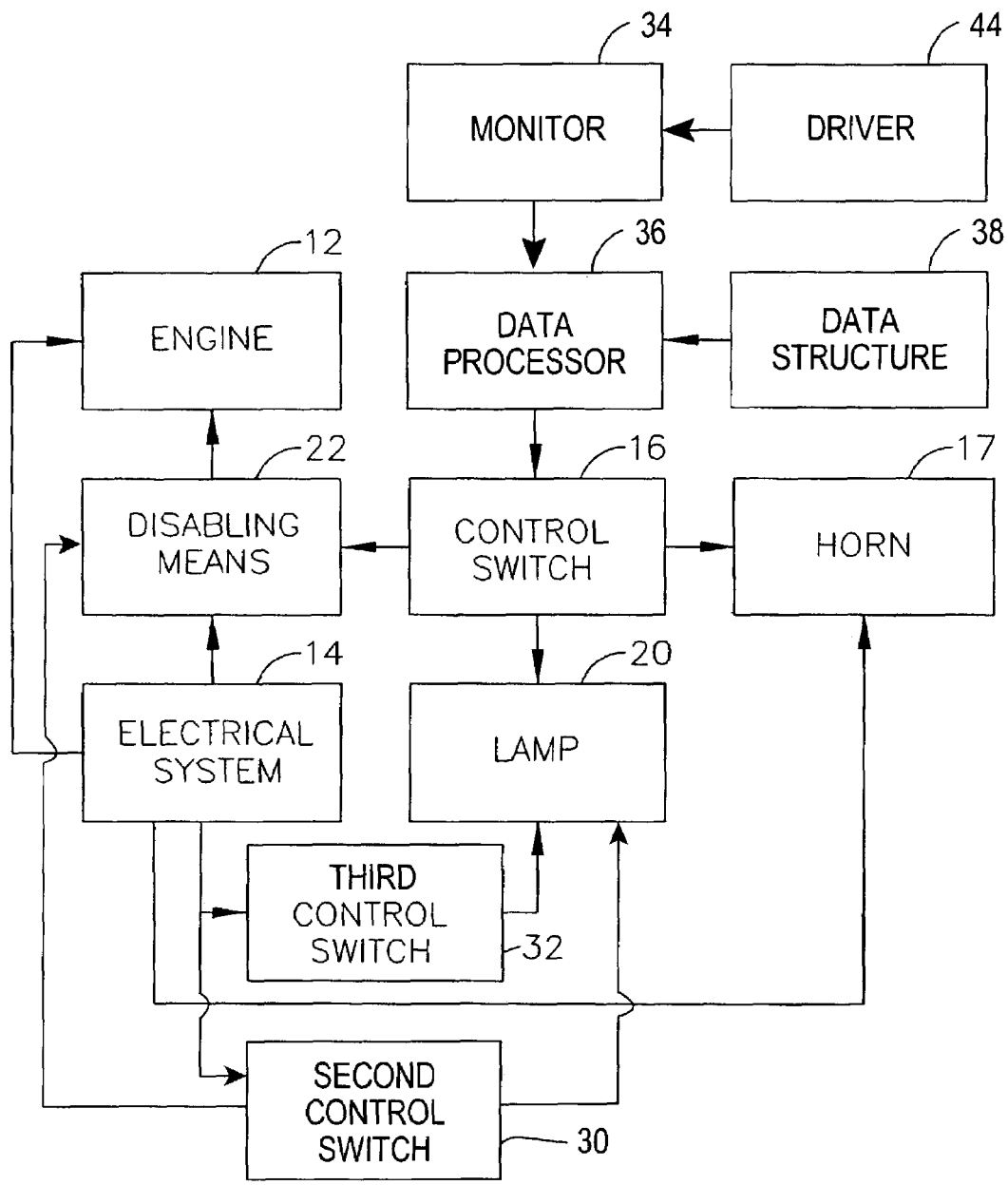
FIG. 4 is a block diagram of an alternate embodiment of the an emergency system.

Referring now to the alternate optional embodiment of FIG. 4, a second control switch 30 electrically communicates with a lamp 20 and a disabling means 22 and a third control switch 32 electrically communicates only with a lamp 20. While two switches 30, 32 are shown in FIG. 4, it can be appreciated that the switches 30, 32 could be replaced with a multicontact switch where different contacts of the single switch control (a) the lamp 20 only and (b) the lamp 20 and the disabling means 22.

Again, the disabling means 22 may take many different forms including a fuel cutoff valve or a means for inhibiting the electrical system 14 from sending electricity to the spark plugs. In the embodiment of FIG. 4, there are provided three modes of use. In a first mode of use, specifically directed for use when a driver is disabled or incapacitated, a control switch 16 automatically controls the disabling means 22 and, optionally a lamp 20, in response to signals received from a data processor 36 based on data received from a monitor 34. In a second mode, a second control switch 30 may be manually actuated to activate the lamp 20 and simultaneously activate the disabling means 22. In a third mode of use, a third control switch 32 may be actuated to activate only the lamp 20. In this fashion, the third mode of use may be used when the driver wishes to maintain control of the motor vehicle 10, i.e. not disable the motor vehicle 10, yet alert other drivers to a hazard condition such as inclement weather, traffic stoppage, hazardous road conditions or the like. As with the second mode of operation, in the third mode of operation, the lamp 20 illuminates, optionally in a blinking fashion, to warn oncoming traffic and trailing traffic in response to actuation of the third control switch 32. Again, the optional embodiment of FIG. 4 could optionally include connections to the motor vehicle's 10 horn 17 from the control switch 16, the second control switch 30, third control switch 32, or all three.

The system of the present invention could be installed into the motor vehicle as it is manufactured or, alternatively, as an aftermarket kit. While some components may be more appropriate for manufacturer installation, it is contemplated that other components could be installed by a motor vehicle owner as a part of a kit.

While certain embodiments of the present invention have been shown and described it is to be understood that the present invention is subject to many modifications and changes without departing from the spirit and scope of the claims presented herein.

I claim:

1. An emergency system for a motor vehicle of the type having an engine providing power to the drive wheels of the motor vehicle and an electrical system, said motor vehicle being operated by a driver in a passenger compartment, comprising:
  a control switch;
  a data processor communicating with and controlling said control switch, said data processor including an associated data structure storing baseline standards;
  a monitor communicating with said data processor and said driver, said monitor collecting data from said driver and transmitting said data to said data processor;
  means for disabling the motor vehicle electrically communicating with said control switch such that said data processor compares the data transmitted by said monitor to said data processor to said stored baseline standards and actuates said control switch to disable the motor vehicle when the comparison indicates a deviation of said data from said baseline standards; and
  an internal lamp mounted in the interior passenger compartment of said motor vehicle electrically connected to the motor vehicle's electrical system and actuatable by said control switch, said data processor actuating the control switch to activate said lamp thereby illuminating interior of the motor vehicle simultaneous with the activation of said disabling means.

2. The system of claim 1 further comprising:
  a second control switch electrically communicating with said lamp and said disabling means that is manually actuatable to simultaneously activate said lamp and disable the engine of the motor vehicle.

3. The system of claim 1 further comprising:
  a third control switch electrically communicating with said lamp that is manually actuatable to activate said lamp only.

4. The system of claim 1 in which said motor vehicle further includes a fuel system directing fuel into said engine for combustion, wherein said disabling means comprises a fuel cutoff switch in said fuel system.

5. The device of claim 1 in which said motor vehicle further comprises a braking system connected to one or more wheels of the motor vehicle, wherein said disabling means comprises brake actuators in said braking system.

6. The device of claim 1 in which said electrical system communicates with said engine, the disabling means comprising a switch to stop the flow of electricity from said electrical system to said engine.

7. The device of claim 1 in which said motor vehicle further comprises a steering wheel in contact with said driver, said monitor being embedded in said steering wheel.

8. The device of claim 1 in which said motor vehicle further comprises a seat belt in contact with said driver, said monitor being embedded in said seat belt.

9. The device of claim 1 in which said motor vehicle further comprises a seat in contact with said driver, said monitor being embedded in said seat.

10. An emergency system for a motor vehicle of the type having an engine providing power to the drive wheels of the motor vehicle and an electrical system, said motor vehicle being operated by a driver in a passenger compartment, comprising:
  a control switch;
  a data processor communicating with and controlling said control switch, said data processor including an associated data structure storing baseline standards;
  a monitor communicating with said data processor and said driver, said monitor collecting data from said driver and transmitting said data to said data processor;
  an internal lamp mounted in the interior passenger compartment of said motor vehicle electrically connected to the motor vehicle's electrical system and actuatable by said control switch, said lamp illuminating the interior of the motor vehicle; and
  means for disabling the motor vehicle electrically communicating with said control switch such that said data processor compares the data transmitted by said monitor to said data processor to said stored baseline standards and actuates said control switch to simultaneously activate said lamp and disable the motor vehicle when the comparison indicates a deviation of said data from said baseline standards.

11. The system of claim 10 further comprising:
a second control switch electrically communicating with said lamp and said disabling means that is manually actuatable to simultaneously activate said lamp and disable the engine of the motor vehicle.

12. The system of claim 10 further comprising:
a third control switch electrically communicating with said lamp that is manually actuatable to actuate the lamp only.

13. The system of claim 10 in which said motor vehicle further includes a fuel system directing fuel into said engine for combustion, wherein said disabling means comprises a fuel cutoff switch in said fuel system.

14. The device of claim 10 in which said motor vehicle further comprises a braking system connected to one or more wheels of the motor vehicle, wherein said disabling means comprises brake actuators in said braking system.

15. The device of claim 10 in which said electrical system communicates with said engine, the disabling means comprising a switch to stop the flow of electricity from said electrical system to said engine.

16. The device of claim 10 in which said motor vehicle further comprises a steering wheel in contact with said driver, said monitor being embedded in said steering wheel.

17. The device of claim 10 in which said motor vehicle further comprises a seat belt in contact with said driver, said monitor being embedded in said seat belt.

18. The device of claim 10 in which said motor vehicle further comprises a seat in contact with said driver, said monitor being embedded in said seat.

19. An emergency system for a motor vehicle of the type having an engine providing power to the drive wheels of the motor vehicle and an electrical system, said motor vehicle being operated by a driver in a passenger compartment, comprising:

a control switch;

a data processor communicating with and controlling said control switch, said data processor including an associated data structure storing baseline standards;

a monitor communicating with said data processor and said driver, said monitor collecting data from said driver and transmitting said data to said data processor;

an internal lamp mounted in the interior passenger compartment of said motor vehicle electrically connected to the motor vehicle's electrical system and actuatable by said control switch, said lamp illuminating the interior of the motor vehicle;

means for disabling the motor vehicle electrically communicating with said control switch such that said data processor compares the data transmitted by said monitor to said data processor to said stored baseline standards and actuates said control switch to simultaneously activate said lamp and disable the motor vehicle when the comparison indicates a deviation of said data from said baseline standards; and a second control switch electrically communicating with said lamp and said disabling means that is manually actuatable to simultaneously activate said lamp and disable the engine of the motor vehicle.

* * * * *